United States Patent [19]

Benjamin

[11] Patent Number: 4,857,043
[45] Date of Patent: Aug. 15, 1989

[54] APPARATUS AND METHODS FOR MEASURING PULSATILE BLOOD PROCESS STREAM PRESSURE

[75] Inventor: Grant S. Benjamin, Costa Mesa, Calif.

[73] Assignee: Baxter Travenol Laboratories, Inc., Deerfield, Ill.

[21] Appl. No.: 125,100

[22] Filed: Nov. 25, 1987

[51] Int. Cl.[4] ............................................. A61M 37/00
[52] U.S. Cl. ....................................... 604/6; 128/674; 73/700; 210/782
[58] Field of Search ................... 604/5, 6, 9; 210/782; 73/756, 706, 700; 128/674, 675

[56] References Cited

U.S. PATENT DOCUMENTS

Re. 29,346  8/1977  Kopp ........................................ 604/5
3,908,653   9/1975  Kettering ................................ 604/5

*Primary Examiner*—Stephen C. Pelligrino
*Attorney, Agent, or Firm*—Nixon & Vanderhye

[57] ABSTRACT

A positive gauge blood pressure signal is transmitted to a gas column from a pulsatile blood flow stream hydrostatically higher than the pressure transducer. Particularly, a first conduit having a predetermined internal diameter smaller than a second conduit is connected at one end to the blood flow stream. The first conduit extends to a turnaround below the pressure transducer and is connected to the second conduit. The opposite end of the second conduit connects with the pressure transducer. The small internal diameter of the first conduit maintains the meniscus of the blood intact notwithstanding the pulsatile blood stream.

17 Claims, 2 Drawing Sheets

APPARATUS AND METHODS FOR MEASURING PULSATILE BLOOD PROCESS STREAM PRESSURE

BACKGROUND AND SUMMARY OF THE INVENTION

The present invention generally relates to hemapheresis apparatus and methods and particularly relates to apparatus and methods for the transmission of a positive gauge liquid pressure signal to a gas column from a pulsatile blood flow stream which is hydrostatically higher than the gas column, while maintaining the gas/blood meniscus.

In blood processing systems, it is usually necessary to monitor certain process stream pressures asceptically and continuously. This monitoring is typically done with a blood column to air column interface where the monitoring point is hydrostatically lower than the transducer. For example, there has recently been developed an instrument which provides for alternate blood collection and packed cell reinfusion cycles through a single needle, while simultaneously and continuously separating whole blood into packed cells and cell-free plasma. In such system, there is provided a hemapheresis instrument comprised of a series of microprocessor-controlled pumps, clamps, sensors and detectors on the face of the instrument, onto which a harness or tubing set is applied. The harness set includes a venepuncture needle, a reservoir, a separator and ancillary tubing for measuring pressures at various locations in the harness set after it is applied to the instrument face and during operation. In that system, the transmembrane pressure, i.e., the pressure across the filter membrane, is measured as a function of the pressure at the inlet port and which measurement is taken at an elevation below the pressure transducer. To effect the measurement, blood at the pressure monitoring location flows in a conduit, as in a manometer, and traps a column of air, the pressure of which is measured at the pressure transducer. To ensure asceptic conditions, a liquid or blood sensor is interposed between the blood/air interface of the conduit ahead of the pressure transducer such that, should blood be detected, the system can be shut down. This blood sensor, however, requires a tubing having sufficient cross-section to enable the sensor to generate a signal.

A system for generating platelet concentrate has been developed wherein it is desirable to monitor the pressure at the output of a separator, i.e., between the separator outlet and a peristaltic pump in such output line. Such system is described and illustrated in co-pending application Ser. No. 07/125,099, filed Nov. 25, 1987, of common assignee herewith. In such system, the pressure monitoring location is higher than the pressure transducer. It is important however, to maintain many of the features of the previously described system in this newer system. Consequently, for this hemapheresis system to transmit a pressure signal from a pressure monitoring location higher in elevation than the pressure measuring point while maintaining and air/blood interface, the system must be asceptic, must transmit air to an air column, the pressure of which could then be measured, must be compatible with a liquid sensor in the air column to preclude liquid or blood from reaching the pressure transducer, and must operate such that a wide range of both positive and negative pressures can be measured.

With reference to FIGS. 2A and 2B hereof, it was initially believed that simply running tubing, as in a manometer, from the elevated pressure monitoring point designated PMP to the lower liquid sensor LS and pressure transducer PT would enable the pressure of the pulsatile blood at the monitoring location to be measured while maintaining the air column between the air/blood interface and the pressure transducer. However, the standard tubing used, i.e., tubing having an interval diameter of 0.125 inches, allowed blood to flow along the side of the downwardly sloping portion of the tubing as indicated at 2 in FIG. 2A and fill the tubing at its lower U-bend. This trapped a pocket of air A behind the charge or slug S1 of blood. When the pressure was relieved, as frequently occurs in this process, this blood slug moved back up toward the process stream. On subsequent pressure increases, second and additional air slugs S2, S3, etc., as illustrated in FIG. 2B, would form and eventually the multiple sequential air/blood slugs formed in the tubing moved upline to the liquid sensor LS. That is, while the total volume of air in the line remained constant, it became dispersed between the blood slugs S enabling the leading blood/air slug S1 to finally reach the liquid sensor. Additionally, it was noted that the pulsations from the peristaltic pump broke down the meniscus in the downline of the tubing, allowing the blood to flow along the inside wall of the tubing thereby forming the air/blood slugs. Consequently, a substantial problem developed in efforts to monitor the pressure of the blood stream adjacent the output of the separator at an elevation above the pressure transducer.

The present invention is directed to apparatus and methods for transmitting the pressure signal from the monitoring location to a pressure transducer located at a lower elevation, while maintaining the gas/blood interface necessary to support the air column by which the pressure measurement is made. To accomplish this, it was recognized that a predetermined volume of gas had to reside in the upline tubing and the pressure transducer to enable the gas/blood interface to act as a piston compressing the air until dynamic equilibrium existed. Additionally, it was recognized that over the range of pressures which were to be measured, an excessive length of constant diameter tubing would be necessary to enable compression of the gas column. This also allowed blood to run down the downline and fill the trap or turnaround point thereby forming gas/blood slugs which, after several pressure cycles, would reach the liquid detector.

It was then recognized that the downline volume could be minimized to move the blood to the turnaround point after a much lower system pressure change. Thus, the downline tubing internal diameter was reduced, in comparison with the internal diameter (I.D.) of the upline, between the monitoring point to a location just beyond the turnaround point. Consequently, the downline would fill with blood with a very small pressure change. It was also recognized that such smaller diameter of the downline tubing enabled the meniscus to remain intact, even with the pressure pulses resulting from the peristaltic pump, and further that the internal diameter (I.D.) of the upline tubing could remain sufficiently large to accommodate the range of measurable pressure requirements of the liquid detector. Therefore, by providing a downline having a substantially smaller internal diameter than the upline, the meniscus is strengthened through an increase in the surface tension of the blood vis-a-vis the tubing, and the sensitivity of the liquid sensing detector is accommodated. Accordingly, the pulsatile blood pressure at the monitoring point, located at an elevation above the pressure transducer, may be transmitted to an air column at the pressure transducer, by using a smaller internal diameter downline connected with a larger internal diameter upline, the transition taking place at an elevation at least level with the turnaround point or higher on the upline tubing.

It was further discovered that a Y-connector at the juncture of the smaller internal diameter downline and the larger internal diameter upline may be used. In such system, the smaller pressure changes could be monitored while the meniscus remained intact as the blood moved into the downline. Numerous cycles of pressure demonstrated that this configuration also provided the required gas/blood separation. The Y-fitting configuration hereof is significant in that it enables the downline and upline of the harness sets to run parallel one to the other thereby facilitating manufacture of the harness set and application of the harness set to the instrument.

Accordingly, in a preferred embodiment of the present invention, there is provided apparatus for transmitting a positive gauge liquid pressure signal to a gas column from a pulsatile fluid stream at a pressure monitoring location hydrostatically higher than the pressure transducer, comprising a first conduit in communication at one end with the fluid stream at the pressure monitoring location for transmission of the fluid therethrough, and having a predetermined internal diameter of a size sufficient to maintain the meniscus of the fluid intact as the fluid flows through the first conduit. A second conduit is provided in communication at one end with the opposite end of the first conduit and in communication at its opposite end with the pressure transducer for containing the gas column, the second conduit having a predetermined internal diameter greater than the internal diameter of the first conduit. The first and second conduits are disposed such that a portion of the first conduit lies below the pressure transducer and substantially reverses direction before connecting with the second conduit whereby the pressure of the gas in the second conduit at the pressure transducer provides a direct measurement of the pressure of the pulsatile fluid stream at the monitoring location without passing fluid into the pressure transducer. Preferably, a U-bend is provided the first conduit upon its reversal. Alternately, however, a Y-connector may be provided at the turnaround of the first conduit with the third passage of the Y-connector being plugged.

In another aspect of the present invention, there is provided a method for transmitting a positive gauge liquid pressure signal to a gas column from a pulsatile fluid stream at a pressure monitoring location hydrostatically higher than the pressure transducer, comprising the steps of providing a first conduit in communication at one end with the fluid stream at the pressure monitoring location for transmission of the fluid therethrough, providing the first conduit with a predetermined internal diameter of a size sufficient to maintain the meniscus of the fluid intact as the fluid flows through the first conduit, providing a second conduit in communication at one end with the opposite end of the first conduit and in communication at its opposite end with the pressure transducer for containing the gas column, providing the second conduit with a predetermined internal diameter greater than the internal diameter of the first conduit, disposing the first and second conduits such that a portion of the first conduit lies below the pressure transducer and substantially reverses direction before connecting with the second conduit and measuring the pressure of the gas in the second conduit at the pressure transducer to provide a direct measurement of the pressure of the pulsatile fluid stream at the monitoring location without passing fluid into the pressure transducer.

Accordingly, it is a primary object of the present invention to provide novel and improved apparatus and methods for the transmission of a positive gauge liquid pressure signal to a gas column from a pulsatile blood flow stream which is hydrostatically higher than the gas column, while maintaining the gas/blood meniscus.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to the present preferred embodiment of the present invention, an example of which is illustrated in the accompanying drawing FIGS. 1, 3 and 4.

Figure 1:
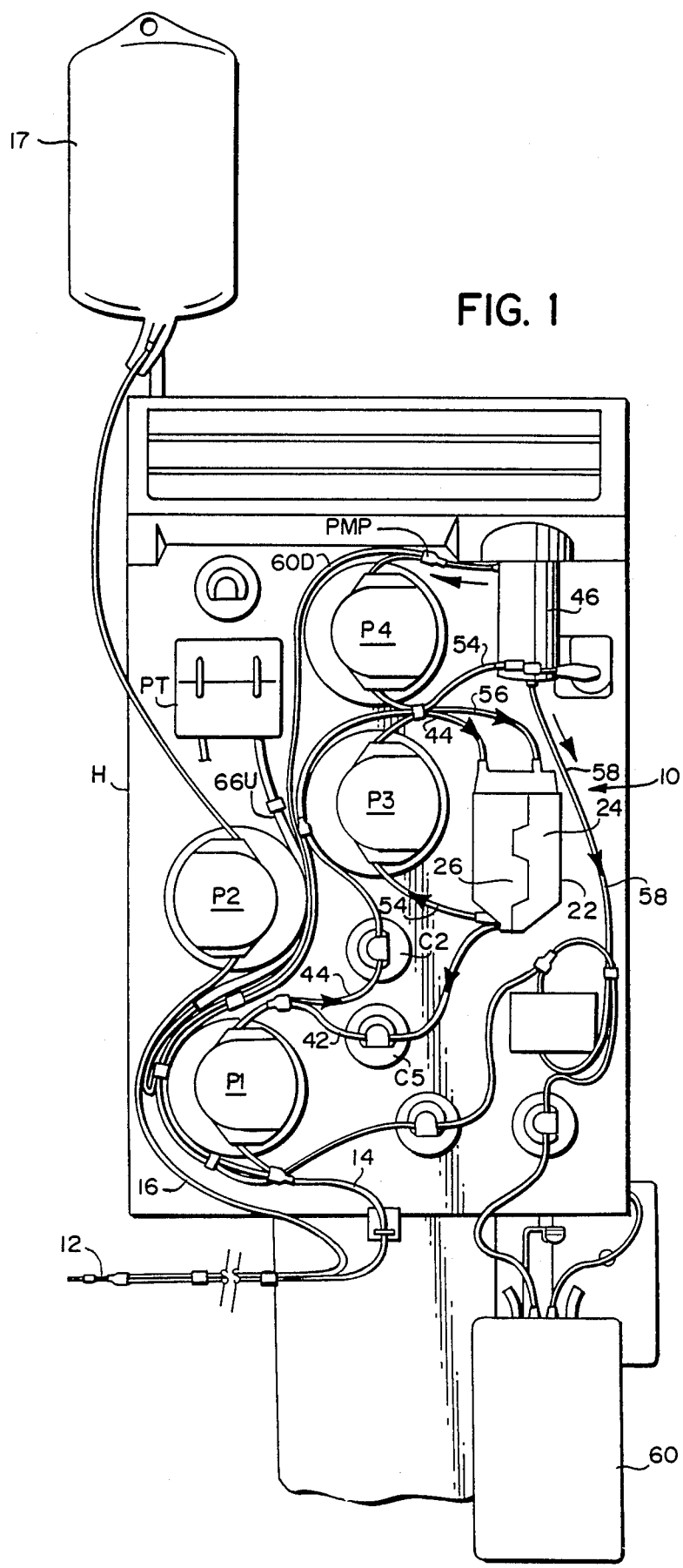
FIG. 1 is a front elevational view of a hemapheresis instrument with a harness set applied illustrating a pressure monitoring point located at the outlet of the separator at an elevation above the pressure transducer for measuring the pressure at the monitoring point.
Figures 2A, 2B:
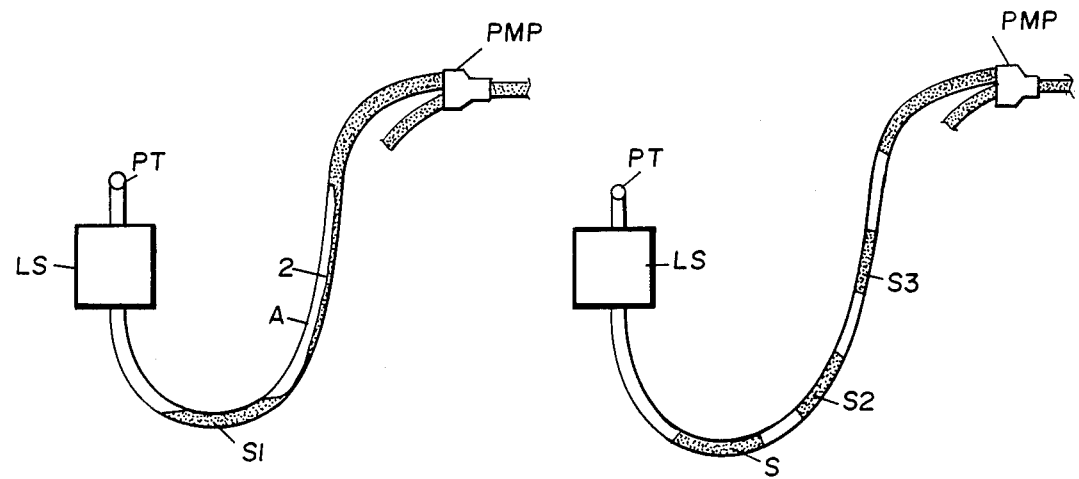
FIGS. 2A and 2B are schematic drawings illustrating certain of the problems solved by the present invention.

Referring now to the drawings, particularly to FIG. 1, there is illustrated a tubing or harness set, generally designated 10, applied to a microprocessor-controlled hemapheresis instrument H in a manner to effect collection of whole blood from a donor through a single needle, separation of the whole blood into packed blood cells and platelet-rich plasma, reinfusion of the packed blood cells to the donor, and subsequent separation of platelets from the platelet-rich plasma to provide platelet concentrate. This system, with the exception of the present invention, is described in detail in co-pending U.S. patent application Ser. No. 125,099, filed 11-25-87, entitled "Apparatus and Methods for Generating Platelet Concentrate", of common assignee herewith, and incorporated in this application by reference thereto. Briefly, however, harness set 10 includes a single venepuncture needle set 12 for receiving whole blood from a donor and reinfusing packed cells, a blood line 14, an anticoagulant line 16 for communication between a supply 17 of anticoagulant and blood line 14, branch blood lines 42 and 44, a dual compartment reservoir 22 having compartments 24 and 26, a separator 46 connected to reservoir compartment 24 via tubing 56 and a platelet-rich plasma collection bag 60 via a tubing 58. Tubing 54 connects the lower end of compartment 26 with the lower inlet to separator 46. A pressure transducer line 60 connects at a Y-connection with the tubing 56 terminating and extends downwardly for connection and communication with a pressure transducer upline 66 which connects with pressure transducer PT. The pressure transducer has a liquid sensor, not shown in this drawing figure, upstream of the pressure measuring transducer PT.

The instrument H includes a series of pumps P1-P4, clamps C2 and C5 and various other sensors and elements which need not be described for purposes of understanding the present invention. In operating the hemapheresis apparatus of FIG. 1, the clamps C2 and C5 are opened and closed, respectively, and the pumps are actuated such that whole blood supplied from a donor through a needle 12 is anticoagulated, and pumped into reservoir compartment 26 via blood line 14 and branch line 44. Pump P3 supplies blood via line 54 into the inlet of separator 46. Packed cells are supplied from the separator outlet via line 56 into compartment 24 for storage during the blood collection cycle. Platelet-rich plasma is drawn from separator 46 via line 58 for collection in bag 60. In that invention, the collection and reinfusion cycles alternate, while the separator 46 continuously separates blood into its constituents. To reinfuse, clamps C2 and C5 are closed and opened, respectively, pump P1 is reversed, pump P2 is stopped and pumps P3 and P4 continue operation. Consequently, packed cells flow from reservoir 24 via lines 42 and 14 to the needle 12 for reinfusion in the donor while separation continues, with blood being continuously supplied from compartment 26 via line 54 and pump P3.

In accordance with the present invention, it is desirable to measure the pressure of the packed blood cells output from separator 46 immediately prior to pump P4, for example at the pressure monitoring point PMP. It will be appreciated from a review of FIG. 1 that such pressure monitoring point PMP is located at an elevation higher than the pressure transducer PT. It will also be appreciated that pump P4 imparts a pulse to the packed cells flowing from separator 46 which, as previously explained, would cause the formation of multiple air/blood slugs S1, S2, S3, etc., in the downline 60 and the upline 66 which ultimately would be detected at the liquid sensor, shutting down the system.

In accordance with the present invention, there is provided downline and upline pressure transmission conduits 60D and 66U, respectively, of different diameters. Specifically, there is provided a downline conduit 60D having an internal diameter smaller than the internal diameter of the upline 66U. In this manner, the positive gauge blood pressure signal may be transmitted to the air column in upline 66U from pulsatile blood in line 56 at point PMP, which is hydrostatically higher than the air column without the problems and with the attendant advantages noted previously.

Figures 3, 4:
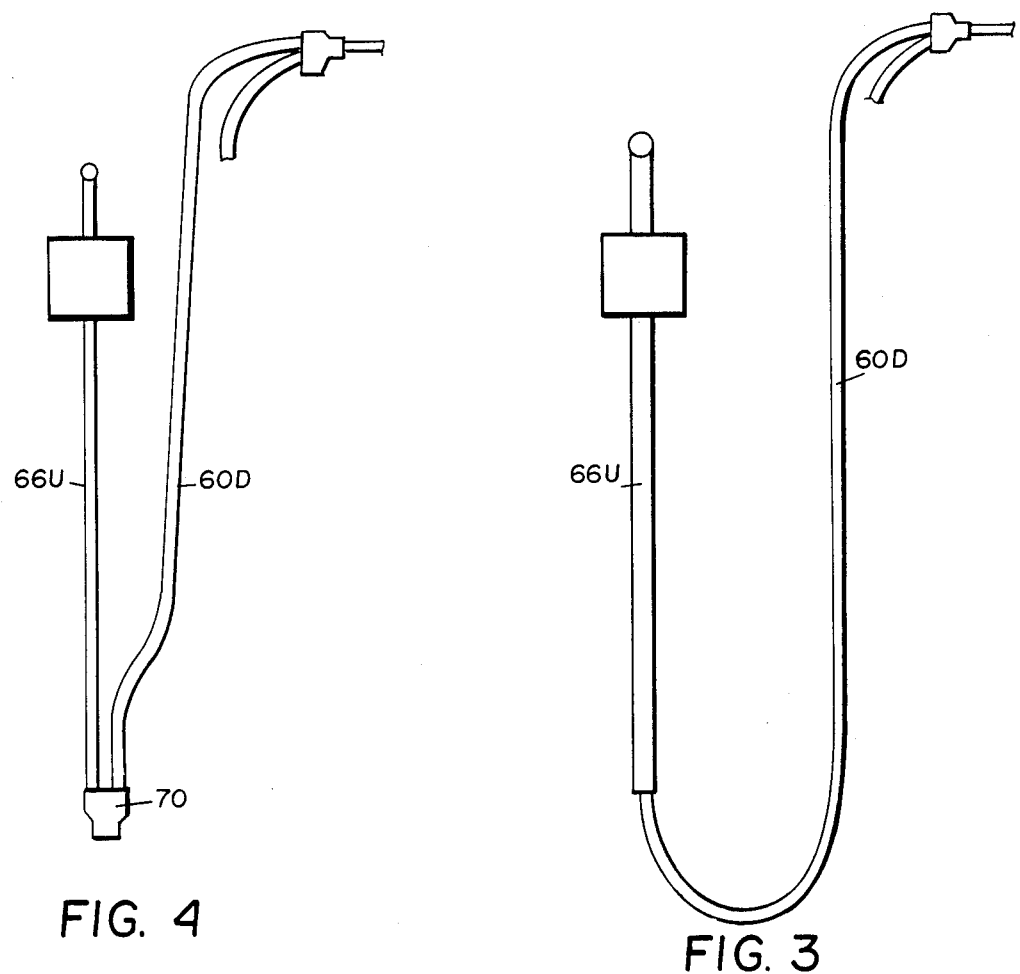
FIG. 3 is a schematic illustration of a pressure measuring system hereof according to the present invention.
FIG. 4 is a further embodiment of the pressure measuring system according to the present invention.

In accordance with this invention, the downline 60D in FIG. 3 may have an internal diameter on the order of 0.040 inches, while the internal diameter of the upline 66U may be about 0.125 inches. Thus, the downline internal volume is 0.008 cc per cm of length, whereas the internal diameter of the upline tubing affords a volume of about 0.079 cc per cm. The junction point between the downline 60D and upline 66U must be on the upline side of the U-bend. With these dimensional relationships, the downline fills with blood, with a pressure change of only 70 mmHg. Importantly, by rendering the I.D. of downline 60D small, the meniscus in the downline remains intact notwithstanding the pressure pulses from peristaltic pump P4. Also, the provision of a smaller I.D. downline enables measurement within the desired pressure range and affords desired sensitivity to the pressure changes. Additionally, it avoids the formation of blood/air slugs by maintaining the meniscus through increased surface tension. Moreover, the system enables the liquid sensor to sense liquid in the upline through the use of tubing having an internal diameter sufficiently large such that the sensor is sensitive to the liquid in the tubing. In short, an internal diameter of about 0.125 inches in the upline is maintained such that the liquid sensor remains sensitive to any liquid in tubing 66U.

In another form of the present invention, illustrated in FIG. 4, there is provided a Y-fitting 70 between the different internal diameter tubings of the downline and upline, respectively. In this form, Y-fitting 70 is used to interconnect the downline and upline such that the two lines may run parallel one to the other in the harness set and thereby minimize the space necessary to accommodate these lines on the instrument face.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for transmitting a positive gauge liquid pressure signal to a gas column from a pulsatile fluid stream at a pressure monitoring location hydrostatically higher than a pressure transducer used to measure pressure in the gas column, comprising;

a first conduit in communication at one end with the fluid stream at the pressure monitoring location for transmission of the fluid therethrough, said first conduit having a predetermined internal diameter of a size sufficient to maintain the meniscus of the fluid intact as the fluid flows through the first conduit;

a second conduit in communication at one end with the opposite end of said first conduit and in communication at its opposite end with the pressure transducer for containing the gas column, said second conduit having a predetermined internal diameter greater than the internal diameter of said first conduit;

said first and second conduits being disposed such that a portion of said first conduit lies below the pressure transducer and substantially reverses direction before connecting with said second conduit whereby the pressure of the gas in the second conduit at the pressure transducer provides a direct measurement of the pressure of the pulsatile fluid stream at the monitoring location without passing fluid into the pressure transducer.

2. Apparatus according to claim 1 in combination with said pressure transducer.

3. Apparatus according to claim 2 wherein said first and second conduits extend substantially vertically relative to one another with said pressure transducer disposed at an elevation intermediate said first conduit portion and the one end of said first conduit.

4. Apparatus according to claim 1 in combination with a harness for application to a hemapheresis instrument, said harness including a venepuncture needle, a separator for separating the blood into first and second constituents, means for supplying blood between said needle and said separator, said first and second conduits and means for flowing blood constituents from said separator, the fluid stream constituting the blood contained in one of said supply means and said flow means with said first blood conduit being in communication with said one supply means or said flow means.

5. Apparatus for transmitting a positive gauge liquid pressure signal to a gas column from a pulsatile fluid stream at a pressure monitoring location hydrostatically higher than a pressure transducer used to measure pressure in the gas column, comprising:
   a first fluid conduit in communication at one end with the fluid stream at the pressure monitoring location for transmission of the fluid therethrough, said first conduit having a predetermined internal diameter of a size sufficient to maintain the meniscus of the fluid intact as the fluid flows through the first conduit;
   a turnaround Y-connector having inlet and outlet ports and a chamber therebetween, the opposite end of said first conduit being connected to said inlet port;
   a second fluid conduit in communication at one end with said outlet port of said Y-connector and in communication at its opposite end with the pressure transducer for transmission of the fluid and for containing the gas column, and second conduit having a predetermined internal diameter greater than the internal diameter of said first conduit;
   said first and second conduits and said Y-connector being disposed such that a portion of said first conduit and said Y-connector lie below the pressure transducer whereby the pressure of the gas in the second conduit at the pressure transducer provides a direct measurement of the pressure of the pulsatile fluid stream at the monitoring location without passing fluid into the pressure transducer.

6. Apparatus according to claim 5 in combination with said pressure transducer, said first and second conduits extending substantially vertically relative to one another with said pressure transducer disposed at an elevation intermediate said Y-connector and said one end of said first conduit.

7. Apparatus according to claim 5 in combination with a harness for application to a hemapheresis instrument, said harness including a venepuncture needle, a separator for separating the blood into first and second constituents, means for supplying blood between said needle and said separator, said first and second conduits, said Y-connector, and means for flowing blood constituents from said separator, the fluid stream constituting the blood contained in one of said supply means and said flow means with said first blood conduit being in communication with said one supply means or said flow means.

8. Apparatus for separating blood into constituents, comprising:
   a separator;
   a phlebotomy needle;
   a pressure transducer;
   a fluid conduit means for supplying blood from said needle to said separator;
   a pump for transmitting blood along said fluid conduit means and affording a pulsatile blood pressure therein at an elevation along said fluid conduit means higher than said pressure transducer;
   means for transmitting a positive gauge pressure signal to a gas column from the pulsatile blood stream at a pressure monitoring location at said elevation including a first conduit in communication at one end with the blood stream at the pressure monitoring location for transmitting blood therefrom, said first conduit having a predetermined internal diameter of a size sufficient to maintain the meniscus of the blood intact as the blood flows through the first conduit;
   a second conduit in communication at one end with said first conduit and at its opposite end with said pressure transducer for containing the gas column, said second conduit having a predetermined diameter greater than the internal diameter of said first conduit;
   said first conduit being disposed such that a portion thereof lies below the pressure transducer whereby the pressure of the gas in the second conduit at the pressure transducer provides a direct measurement of the pressure of the pulsatile blood at the monitoring location without passing blood into the pressure transducer.

9. Apparatus according to claim 8 wherein said first and second conduits have internal diameters of about 0.040 inches and about 0.125 inches, respectively.

10. A method for transmitting a positive gauge liquid pressure signal to a gas column from a pulsatile fluid stream at a pressure monitoring location hydrostatically higher than the pressure transducer, comprising the steps of:
    providing a first conduit in communication at one end with the fluid stream at the pressure monitoring location for transmission of the fluid therethrough;
    providing said first conduit with a predetermined internal diameter of a size sufficient to maintain the meniscus of the fluid intact as the fluid flows through the first conduit;
    providing a second conduit in communication at one end with the opposite end of said first conduit and in communication at its opposite end with the pressure transducer for containing the gas column;
    providing said second conduit with a predetermined internal diameter greater than the internal diameter of said first conduit;
    disposing said first and second conduits such that a portion of said first conduit lies below the pressure transducer and substantially reverses direction before connecting with said second conduit; and
    measuring the pressure of the gas in the second conduit at the pressure transducer to provide a direct measurement of the pressure of the pulsatile fluid stream at the monitoring location without passing fluid into the pressure transducer.

11. A method according to claim 10 including the steps of disposing the first and second conduits to extend substantially vertically relative to one another and disposing said pressure transducer at an elevation intermediate said first conduit portion and the one end of said first conduit.

12. A method according to claim 10 including the steps of providing a hemapheresis harness, having a venepuncture needle, a separator for separating blood into first and second constituents, means for supplying blood between said needle and said separator, said first and second conduits and means for flowing blood constituents from said separator, providing a hemapheresis instrument having a pressure transducer, and applying the harness to the instrument, the fluid stream constituting the blood contained in one of said supply means and said flow means with said first blood conduit being in communication with said one supply means or said flow means.

13. A method according to claim 10 including the step of disposing a liquid sensor at a location in said second conduit to detect liquid therein before any liquid flows to the pressure transducer.

14. A method for transmitting a positive gauge liquid pressure signal to a gas column from a pulsatile fluid stream at a pressure monitoring location hydrostatically higher than a pressure transducer used to measure pressure in the gas column, comprising the steps of:
   providing a first conduit in communication at one end with the fluid stream at the pressure monitoring location for transmission of the fluid therethrough;
   providing said first conduit with a predetermined internal diameter of a size sufficient to maintain the meniscus of the fluid intact as the fluid flows through the first conduit;
   providing a turnaround Y-connector having inlet and outlet ports and a chamber therebetween, the opposite end of said first conduit being connected to said inlet port;
   providing a second conduit in communication at one end with said outlet port of said Y-connector and in communication at its opposite end with the pressure transducer for containing the gas column;
   providing said second conduit with a predetermined internal diameter greater than the internal diameter of said first conduit;
   disposing said first and second conduits and said Y-connector such that a portion of said first conduit and said Y-connector lie below the pressure transducer; and
   measuring the pressure of the gas in the second conduit at the pressure transducer to provide a direct measurement of the pressure of the pulsatile fluid stream at the monitoring location without passing fluid into the pressure transducer.

15. A method according to claim 14 including disposing said first and second conduits substantially vertically relative to one another and disposing said pressure transducer at an elevation intermediate said Y-connector and said one end of said first conduit.

16. A method according to claim 10 including the steps of providing a hemapheresis harness having a venepuncture needle, a separator for separating the blood into first and second constituents, means for supplying blood between said needle and said separator, said first and second conduits, said Y-connector, and means for flowing blood constituents from said separator, providing a hemapheresis instrument having a pressure transducer, applying the harness to the instrument, the fluid stream constituting the blood contained in one of said supply means and said flow means with said first blood conduit being in communication with said one supply means or said flow means.

17. A method for separating blood into constituents, comprising:
   providing a separator, a phlebotomy needle and a pressure transducer;
   supplying blood from said needle to said separator through a blood conduit;
   pumping blood along said conduit between said needle and said separator, affording a pulsatile blood pressure in said conduit;
   providing a pulsatile pressure monitoring station at an elevation along said conduit higher than said pressure transducer for transmitting a positive gauge pressure signal to a gas column from the pulsatile blood stream;
   providing a first conduit in communication at one end with the blood stream at the pressure monitoring station for transmitting blood therefrom;
   providing said first conduit with a predetermined internal diameter of a size sufficient to maintain the meniscus of the blood intact as the blood flows through the first conduit;
   providing a second fluid conduit in communication at one end with said first conduit and at its opposite end with said pressure transducer for transmission of the blood and for containing the gas column;
   providing said second conduit with a predetermined diameter greater than the internal diameter of said first conduit,
   disposing said first conduit such that a portion thereof lies below the pressure transducer; and
   measuring the pressure of the gas in the second conduit at the pressure transducer to provide a direct measurement of the pressure of the pulsatile blood at the monitoring location without passing blood into the pressure transducer.

* * * * *

UNITED STATES PATENT AND TRADEMARK OFFICE
CERTIFICATE OF CORRECTION

PATENT NO. : 4,857,043

DATED : August 15, 1989

INVENTOR(S) : Grant S. Benjamin

It is certified that error appears in the above-identified patent and that said Letters Patent is hereby corrected as shown below:

In claim 10, at column 8, change line 30 to: -- higher than a pressure transducer used to measure pressure in the gas column, comprising the --

Signed and Sealed this

Twelfth Day of March, 1991

Attest:

HARRY F. MANBECK, JR.

*Attesting Officer*   *Commissioner of Patents and Trademarks*